United States Patent [19]

Vanmaele

[11] Patent Number: 5,589,316
[45] Date of Patent: Dec. 31, 1996

United States Patent

[54] DYES AND DYE-DONOR ELEMENTS FOR THERMAL DYE TRANSFER RECORDING

[75] Inventor: Luc Vanmaele, Lochristi, Belgium

[73] Assignee: Agfa-Gevaert N.V., Mortsel, Belgium

[21] Appl. No.: 526,848

[22] Filed: Sep. 11, 1995

[30] Foreign Application Priority Data

Sep. 13, 1994 [EP] European Pat. Off. .............. 94202634

[51] Int. Cl.⁶ ............................ B41M 5/035; B41M 5/38
[52] U.S. Cl. ...................... 430/200; 503/227; 425/195; 425/913; 425/914; 8/471; 430/201; 430/945
[58] Field of Search .................... 8/471; 503/227; 430/201, 200, 945; 156/234, 235; 428/195, 914, 913

[56] References Cited

U.S. PATENT DOCUMENTS

| | | | |
|---|---|---|---|
| 4,153,607 | 8/1979 | Eilingsfeld et al. | 548/153 |
| 5,169,828 | 12/1992 | Janssens et al. | 503/227 |
| 5,229,353 | 7/1993 | Vanmaele et al. | 503/227 |
| 5,254,523 | 10/1993 | Fujimura et al. | 503/227 |
| 5,286,705 | 2/1994 | Kanto et al. | 503/227 |
| 5,306,815 | 4/1994 | Hahn et al. | 503/227 |
| 5,356,857 | 10/1994 | Vanmaele | 503/227 |
| 5,374,601 | 12/1994 | Takiguchi et al. | 503/227 |
| 5,393,725 | 2/1995 | Abe et al. | 503/227 |
| 5,438,122 | 8/1995 | Vanmaele | 534/551 |

*Primary Examiner*—Janet C. Baxter
*Assistant Examiner*—Morton J. Angebranndt
*Attorney, Agent, or Firm*—Brumbaugh, Graves, Donohue & Raymond

[57] ABSTRACT

The present invention provides a dye-donor element for use according to thermal dye sublimation transfer. The dye-donor element comprises a support having thereon a dye layer comprising a polymeric binder and a dye corresponding to the following general formula (I):

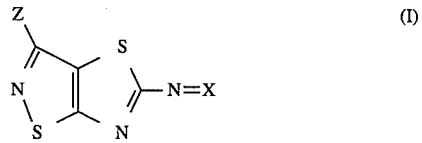

wherein:

Z represents hydrogen or a substituent.

X represents N-R or

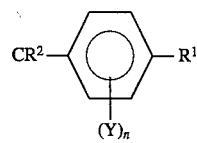

R represents $NR^3R^4$ or the residue of an aromatic coupling compound E-Q wherein Q is a group displaceable by a diazotized amine:

$R^1$ represents $NR^3R^4$, $OR^{12}$ or $SR^{12}$;

$R^2$ represents hydrogen, cyano, $COR^{13}$, $CO_2R^{13}$, $CONR^{14}R^{15}$, $SO_2R^{16}$;

$R^3$ and $R^4$ each independently represent hydrogen, an alkyl group, an alkenyl group, an alkynyl group, an aryl group, an a heterocyclic group or $R^3$ and $R^4$ together with the atoms to which they are attached represent the atoms necessary to complete a ring:

Y represents a substituent;

n represents 0, 1, 2, 3 or 4, the substituents being the same or different when n is greater than 1 or two or more Y substituents can form an annelated ring system;

$R^{12}$, $R^{13}$, $R^{14}$ and $R^{15}$ each independently represent hydrogen, an alkyl group, an alkenyl group, an alkynyl group, an aryl group, a heterocyclic ring or $R^3$ and $R^4$ together with the atoms to which they are attached represent the necessary atoms to form a 5- or 6-membered ring or $R^3$ and/or $R^4$ together with the atoms to which they are attached and one of the Y-substituents represent the necessary atoms to form a 5- or 6-membered, fused-on heterocyclic ring or $R^{14}$ and $R^{15}$ together with the atoms to which they are attached represent the necessary atoms to form a 5- or 6-membered ring or $R^{13}$ or $R^{14}$ or $R^{15}$ or $R^{14}$ and $R^{15}$ together with one of the Y-substituents and the atoms to which they are attached represent the necessary atoms to form a 5- or 6-membered fused-on heterocyclic ring:

$R^{16}$ represents hydroxy, an alkoxy group, an aryloxy group, $NR^{17}R^{18}$, an aryl group or an alkyl group, an alkenyl group, an alkynyl group, or $R^{16}$ together with one of the Y-substituents and the atoms to which they are attached represent the necessary atoms to form a 5- or 6-membered fused-on heterocyclic ring:

$R^{17}$ and $R^{18}$ each independently represent hydrogen, an alkyl group, an alkenyl group, an alkynyl group, an aryl group, a heterocyclic ring or $R^{17}$ and $R^{18}$ together with the atoms to which they are attached represent the necessary atoms to form a 5- or 6-membered ring.

The present invention further provides a method for making an image using the aforementioned dye donor element.

12 Claims, No Drawings

DYES AND DYE-DONOR ELEMENTS FOR THERMAL DYE TRANSFER RECORDING

DESCRIPTION

1. Field of the Invention

The present invention relates to dye-donor elements for use according to thermal dye sublimation transfer and to novel dyes for use in said dye-donor elements.

2. Background of the Invention

Thermal dye sublimation transfer or thermal dye diffusion transfer is a recording method in which a dye-donor element provided with a dye layer containing sublimable dyes having heat transferability is brought into contact with a receiver sheet or receiver element and selectively, in accordance with a pattern information signal, is heated by means of a thermal printing head provided with a plurality of juxtaposed heat-generating resistors, whereby dye is transferred from the selectively heated regions of the dye-donor element to the receiver sheet and forms a pattern thereon, the shape and density of which are in accordance with the pattern and intensity of heat applied to the dye-donor element.

A dye-donor element for use according to thermal dye sublimation transfer usually comprises a very thin support e.g. a polyester support, one side of which is covered with a dye layer comprising the printing dyes. Usually, an adhesive or subbing layer is provided between the support and the dye layer. Normally, the opposite side is covered with a slipping layer that provides a lubricated surface against which the thermal printing head can pass without suffering abrasion. An adhesive layer may be provided between the support and the slipping layer.

The dye layer can be a monochromic dye layer or it may comprise sequential repeating areas of differently coloured dyes e.g. dyes having a cyan, magenta, yellow, and optionally black hue. When a dye-donor element containing three or more primary colour dyes is used, a multicolour image can be obtained by sequentially performing the dye transfer process steps for each colour.

A primary coloured dye layer e.g. a magenta or cyan or yellow dye layer may comprise only one primary coloured dye (a magenta, cyan or yellow dye respectively) or may comprise a mixture of two or more primary colour dyes of the same hue (two magenta, two cyan or two yellow dyes respectively).

Any dye can be used in such a dye layer provided it is easily transferable to the dye-image-receiving layer of the receiver sheet or element by the action of heat.

Typical and specific examples of dyes for use in thermal dye sublimation transfer have been described in e.g. EP 209,990, EP 209,991, EP 216,483, EP 218,397, EP 227,095, EP 227,096, EP 229,374, EP 235,939, EP 247,737, EP 257,577, EP 257,580, EP 258,856, EP 400,706.EP 279,330. EP 279,467, EP 285,665, U.S. Pat. No. 4,743,582, U.S. Pat. No. 4,753,922, U.S. Pat. No. 4,753,923, U.S. Pat. No. 4,757,046, U.S. Pat. No. 4,769,360, U.S. Pat. No. 4,771,035, U.S. Pat. No. 5,026,677, JP 84/78,894. JP 84/78,895, JP 84/78,896, JP 84/227,490, JP 84/227,948, JP 85/27,594, JP 85/30,391, JP 85/229,787. JP 85/229,789, JP 85/229,790, JP 85/229,791, JP 85/229,792. JP 85/229,793, JP 85/229,795, JP 86/41,596, JP 86/268,493. JP 86/268,494, JP 86/268,495, and JP 86/284,489.

In spite of the many dyes that already exist, there is still a continuous search for novel dyes and especially for dyes that are suited for use in dye-donor elements for thermal dye sublimation transfer printing, preferably dyes with low melting points and a good solubility in ecologically acceptable solvents.

SUMMARY OF THE INVENTION

It is therefore an object of the present invention to provide novel dye-donor elements for use according to thermal dye sublimation transfer printing.

It is another object of the present invention to provide novel dyes that can be used in said dye-donor elements.

Other objects will become apparent from the description hereinafter.

In accordance with the present invention a dye-donor element for use according to thermal dye sublimation transfer is provided. said dye-donor element comprising a support having thereon a dye layer comprising a polymeric binder and at least one dye, wherein said at least one dye corresponds to the following general formula (I):

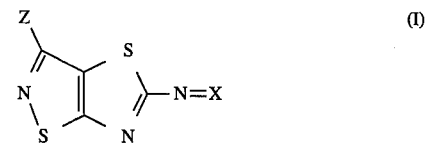

wherein:
Z represents hydrogen or a substituent,
X represents N-R or

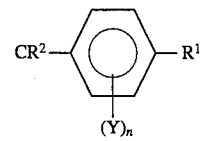

R represents $NR^3R^4$ or the residue of an aromatic coupling compound E-Q wherein Q is a group displaceable by a diazotised amine;

$R^1$ represents $NR^3R^4$, $OR^{12}$ or $SR^{12}$;

$R^2$ represents hydrogen, cyano, $COR^{13}$ $CO_2R^{13}$ $CONR^{14}R^{15}$ $SO_2R^{16}$;

$R^3$ and $R^4$ each independently represent hydrogen, an alkyl group, an alkenyl group, an alkynyl group, an aryl group, a heterocyclic group or $R^3$ and $R^4$ together with the nitrogen atom to which they are attached represent the atoms necessary to complete a ring or $R^3$ and/or $R^4$ and one of the Y-substituents together with the atoms to which they are attached represent the necessary atoms to form a 5- or 6-membered, fused-on heterocyclic ring:

Y represents a substituent. e.g. SH, OH, an amino group, a halogen, CN, $NO_2$, an alkyl group, an alkenyl group, an alkynyl group, an alkoxy group, a thioalkoxy group, a carbamoyl group, a sulfamoyl group, an acylamino group, a sulfonylamino group or a carboxylic ester;

n represents 0, 1, 2, 3 or 4, the substituents being the same or different when n is greater than 1 or two or more Y substituents can form an annelated ring system:

$R^{12}$, $R^{13}$, $R^{14}$ and $R^{15}$ each independently represent hydrogen, an alkyl group, an alkenyl group, an alkynyl group, an aryl group, a heterocyclic ring or $R^{14}$ and $R^{15}$ together with the atoms to which they are attached represent the necessary atoms to form a 5- or 6-membered ring or $R^{13}$ or $R^{14}$ or $R^{15}$ or $R^{14}$ and $R^{15}$ together with one the Y-substituents and the atoms to which they are attached represent the necessary atoms to form a 5- or 6-membered fused-on heterocyclic ring:

$R^{16}$ represents hydroxy, an alkoxy group, an aryloxy group, $NR^{17}R^{18}$, an aryl group or an alkyl group, an alkenyl group, an alkynyl group, or $R^{16}$ together with one of the Y-substituents and the atoms to which they are attached represent the necessary atoms to form a 5- or 6-membered fused-on heterocyclic ring:

$R^{17}$ and $R^{18}$ each independently represent hydrogen, an alkyl group, an alkenyl group, an alkynyl group, an aryl group, a heterocyclic ring or $R^{17}$ and $R^{18}$ together with the atoms to which they are attached represent the necessary atoms to form a 5- or 6-membered ring.

The present invention also provides novel yellow and magenta dyes corresponding to the above general formula I.

According to the present invention there is further provided a method for making an image according to the thermal dye transfer process comprising the steps of:

placing the dye layer of a dye donor element as defined above in face-to-face relationship with a dye-image receiving layer of a receiver sheet:

image-wise heating a thus obtained assemblage and separating said receiver sheet from said dye donor element.

DETAILED DESCRIPTION OF THE INVENTION

In the above formula (I), when X represents N-R wherein R represents the residue of an aromatic coupling compound, the coupler E-Q is preferably of the formula E-H, in which the displaceable group Q, is hydrogen. Preferably E is represented by general formula (II), in which

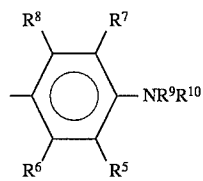

$R^5$, $R^6$, $R^7$, and $R^8$ each independently represent hydrogen, an alkyl group, an alkenyl group, an alkynyl group, an aryl group, an alkoxy group, an alkylthio group, an arylthio group, an aryloxy group, a carbamoyl group, a sulfamoyl group, hydroxy, SH, an amino group, a halogen $NO_2$, CN, $NHSO_2R^{11}$, $NHCOR^{11}$, $OSO_2R^{11}$, $OCOR^{11}$, $COR^{11}$ or $R^7$ and $R^8$ together and/or $R^5$ and $R^6$ together with the atoms to which they are attached represent the necessary atoms to complete a ring or $R^7$ and $R^9$ together with the atoms to which they are attached and/or $R^5$ and $R'0$ together with the atoms to which they are attached represent the necessary atoms to form a heterocyclic ring:

$R^{11}$ represents an alkyl group, an alkenyl group, an alkynyl group, an aryl group, an alkyloxy group, an aryloxy group, an alkylthio group, an arylthio group, an amino group or a heterocyclic group: $R^9$ and $R^{10}$ each independently represent hydrogen, an alkyl group, an alkenyl group, an alkynyl group, an aryl group, a heterocyclic group or $R^9$ and $R'0$ together with the atoms to which they are attached represent the necessary atoms to form a heterocyclic ring.

The variables $R^3$ and $R^4$ in the above formula preferably represent methyl, ethyl, propyl, isopropyl, butyl, sec.butyl, tert.butyl, isobutyl, cyclohexyl, benzyl, cyclopentyl, a phenyl group substituted preferentially in ortho and/or para with methyl, ethyl, halogen, $NO_2$, CN, $SO_2CH_3$, alkoxy such as methoxy, dialkylamino such as dimethylamino, diethylamino and dibutylamino, alkylthio, carboalkoxy such as carbomethoxy and carboethoxy or $R^3$ and $R^4$ together with the atoms to which they are attached form a heterocyclic ring, such as a tetrahydroquinoline ring, a tetrahydroisoquinoline ring, an imidazolyl ring, a pyrazolyl ring, a pyrazolidine ring, a pyrazoline ring, etc.;

A non-exhaustive list of dyes corresponding to the above general formula (I) is given in Table 1, 2 and 3 hereinafter.

TABLE 1

| Dye | $R^3$ | $R^4$ |
|---|---|---|
| T.1 | $C_4H_9$ | $C_6H_5$ |
| T.2 | $C_2H_5$ | $C_6H_5$ |
| T.3 | $C_4H_9$ | $C_6H_4p.CH_3$ |
| T.4 | $C_4H_9$ | $C_6H_4p.N(C_2H_5)_2$ |
| T.5 | $C_4H_9$ | DiMePh |
| T.6 | $C_4H_9$ | DiMeOPh |
| T.7 | $C_2H_5$ | $C_6H_4p.OCH_3$ |
| T.8 | $C_4H_9$ | $C_6H_4p.OCH_3$ |
| T.9 | $C_4H_9$ | $C_6H_4p.SO_2CH_3$ |
| T.10 | $C_4H_9$ | $C_6H_4p.NO_2$ |
| T.11 | $NR^1R^2$ = THQ | |
| T.12 | $NR^1R^2$ = Im | |
| T.13 | $NR^1R^2$ = THIQ | |
| T.14 | $NR^1R^2$ = Pyr | |
| T.15 | $CH(CH_3)C_2H_5$ | $C_6H_4p.CH_3$ |
| T.16 | $CH(CH_3)C_2H_5$ | DiMePh |
| T.17 | $CH_2CH(CH_3)_2$ | $C_6H_4p.CH_3$ |
| T.18 | $C(CH_3)_3$ | DiMePh |
| T.19 | $C_3H_7$ | DiMePh |
| T.20 | $C_3H_7$ | Pyrid |

The meaning of the abreviations used in table 1 are explained hereinafter.

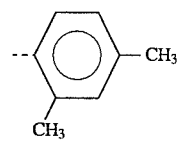

DiMePh

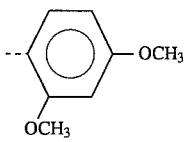

DiMeOPh

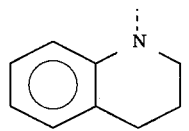

THQ

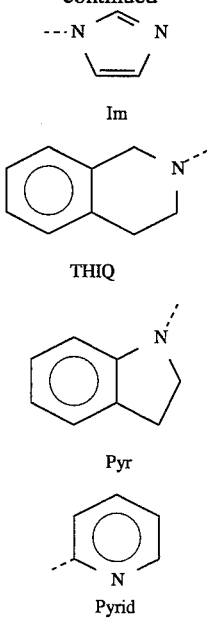

Im

THIQ

Pyr

Pyrid

TABLE 2

| Dye | $R^9$ | $R^{10}$ | $R^6$ | $R^7$ |
|---|---|---|---|---|
| A.1 | $CH_3$ | $CH_3$ | H | H |
| A.2 | $C_2H_5$ | $C_2H_5$ | H | H |
| A.3 | $C_4H_9$ | $C_4H_9$ | H | H |
| A.4 | $C_2H_5$ | $C_4H_9$ | H | H |
| A.5 | $C_2H_5$ | $CH(CH_3)C_2H_5$ | H | H |
| A.6 | $C_4H_9$ | $CH(CH_3)C_2H_5$ | H | H |
| A.7 | $C_4H_9$ | $CH_2CH(CH_3)_2$ | H | H |
| A.8 | $C_4H_9$ | $CH(CH_3)C_2H_5$ | NHAc | H |
| A.9 | $C_4H_9$ | $CH(CH_3)C_2H_5$ | $OCH_3$ | H |
| A.10 | $C_4H_9$ | $CH(CH_3)C_2H_5$ | NHAc | OMe |
| A.11 | $C_4H_9$ | $CH(CH_3)C_2H_5$ | $CH_3$ | $CH_3$ |
| A.12 | $C_4H_9$ | $CH(CH_3)C_2H_5$ | $OCH_3$ | $OCH_3$ |
| A.13 | $C_4H_9$ | $CH(CH_3)C_2H_5$ | NHCOi.Bu | H |
| A.14 | $C_4H_9$ | $CH(CH_3)C_2H_5$ | Cl | H |
| A.15 | $C_4H_9$ | $C_4H_9$ | NHAc | H |
| A.16 | $C_4H_9$ | $CH_2C_6H_5$ | H | H |
| A.17 | $C_2H_5$ | $CH_2C_6H_5$ | H | H |
| A.18 | $C_4H_9$ | $C_4H_9$ | OMe | H |
| A.19 | $C_4H_9$ | EOPh | H | H |
| A.20 | $CH_2CH(CH_3)_2$ | $CH_2CH(CH_3)_2$ | H | H |

A.21

TABLE 2-continued

| Dye | $R^9$ | $R^{10}$ | $R^6$ | $R^7$ |
|---|---|---|---|---|

A.22

A.23

A.24

A.25

The meaning of the abbreviation used in table 2 is follows:

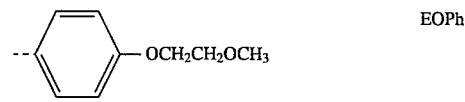

EOPh

TABLE 3

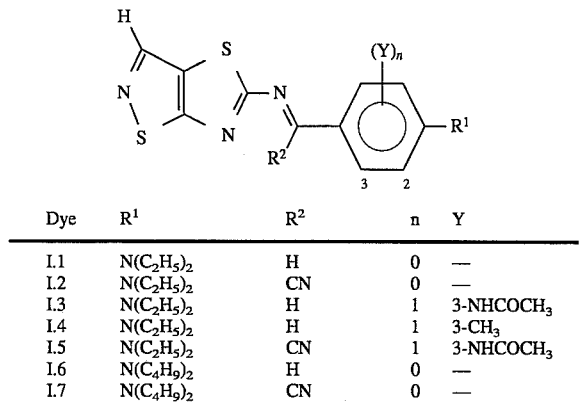

| Dye | $R^1$ | $R^2$ | n | Y |
|---|---|---|---|---|
| I.1 | $N(C_2H_5)_2$ | H | 0 | — |
| I.2 | $N(C_2H_5)_2$ | CN | 0 | — |
| I.3 | $N(C_2H_5)_2$ | H | 1 | 3-NHCOCH_3 |
| I.4 | $N(C_2H_5)_2$ | H | 1 | 3-CH_3 |
| I.5 | $N(C_2H_5)_2$ | CN | 1 | 3-NHCOCH_3 |
| I.6 | $N(C_4H_9)_2$ | H | 0 | — |
| I.7 | $N(C_4H_9)_2$ | CN | 0 | — |

TABLE 3-continued

| Dye | R¹ | R² | n | Y |
|---|---|---|---|---|
| I.8 | N—C₄H₉<br>\|<br>CH(CH₃)C₂H₅ | H | 0 | — |
| I.9 | N—C₄H₉<br>\|<br>CH(CH₃)C₂H₅ | CN | 0 | — |
| I.10 | Mor | H | 0 | — |
| I.11 | Mor | CN | 0 | — |
| I.12 | N(C₂H₅)₂ | CO₂C₂H₅ | 0 | — |
| I.13 | OC₄H₉ | CN | 0 | — |

I.14

I.15

In table 3 the meaning of Mor is as follows:

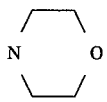

wherein the linking of the group is at the nitrogen.

The synthesis of the dyes according to formula I will become apparent from the examples given below.

EXAMPLE 1

Synthesis of dye A.3

Dye A.3 is prepared according to scheme 1. Dye B is prepared according to known methods such as those described in U.S. Pat. No. 4,395,544 and U.S. Pat. No. 4,505,857.

Scheme 1

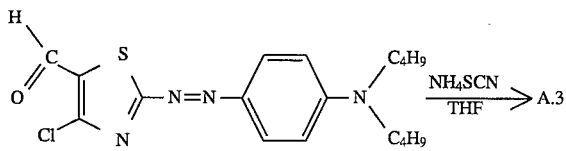

11.4 g (0.03 mole) of dye B and 5.4 g (0.07 mole) of NH₄SCN are dissolved in 100 ml of THF and the solution is refluxed for 3 hours. After cooling 250 ml of CH₂Cl₂ is added and the organic layer is washed with water, dried over MgSO₄ and concentrated under reduced pressure. The resulting oil is purified by column chromatography and compound A.3 is further crystallized from ethyl acetate to obtain 4 g of pure dye A.3 (m.p. 130° C.). The structure of dye A.3 is confirmed by 1H-NMR analysis (20° C., CDCl₃, 300 MHz) : 0.97 ppm (CH₃); 1.38 ppm (CH₂): 1.63 ppm (CH₂); 3.40 ppm (N-CH₂); 6.68, 7.91 ppm (phenyl); 8.62 ppm (H—C=N); 7.29 ppm (CHCl₃), and ¹³C-NMR analysis (CDCl₃, 20° C., 75 MHz) : 13.9; 20.2: 29.5; 51.3; 111.8; 128.5: 129.3; 142.5; 147.7: 153.3; 174.0; 185.0 ppm.

EXAMPLE 2

Synthesis of dye A.15

Dye A.15 is prepared according to scheme 2. Dye C is prepared according to known methods such as described in U.S. Pat. No. 4,395,544 and U.S. Pat. No. 4,505,857.

Scheme 2

8.72 g (0.02 mole) of dye C is suspended in 50 ml of dimethylacetamid. 4.6 g (0.06 mole) of NH₄SCN is added followed by one drop of CH₃SO₃H. The reaction mixture is heated for two hours at 90° C. After cooling the reaction mixture is diluted with water and methanol. The precipitate is filtered and washed with water. After purification by column chromatography 2.1 g of pure dye A.15 is obtained (m.p. 149° C.). The structure of dye A.15 is confirmed by ¹H-NMR analysis (75° C., 300 MHz, DMSO) : 0.98 ppm (CH₃); 1.41 ppm (CH₂); 1.66 ppm (CH₂); 3.51 pm (N—CH₂); 2.23 ppm (CH₃CO); 7.74, 6.74, 7.92 ppm (phenyl); 8.84 ppm (H—C=N): 10.30 ppm (NH); 2.50 ppm (DMSO).

EXAMPLE 3

Synthesis of dye A.18

Dye A.18 is prepared analogously to example 2 (yield: 42%) (m.p.=186° C.). The structure of dye A. 18 is confirmed by ¹H-NMR analysis (CDCl₃, 20° C. 300 MHz) : 1.01 ppm (CH₃); 1 42 ppm (CH₂); 1.67 ppm (CH₂); 3.43 ppm (N—CH₂); 4.03 ppm (OCH₃); 6.10, 6.37, 8.01 ppm (phenyl): 8.60 ppm (H-C=N): 7.28 ppm (CHCl₃).

EXAMPLE 4

Synthesis of dye T.3

Dye T.3 is prepared according to scheme 3. The starting materials D and E can be prepared according to literature procedures known to those who are skilled in the art of organic synthesis, e.g. U.S. Pat. No. 4,395,544 for the preparation of D.

Scheme 3

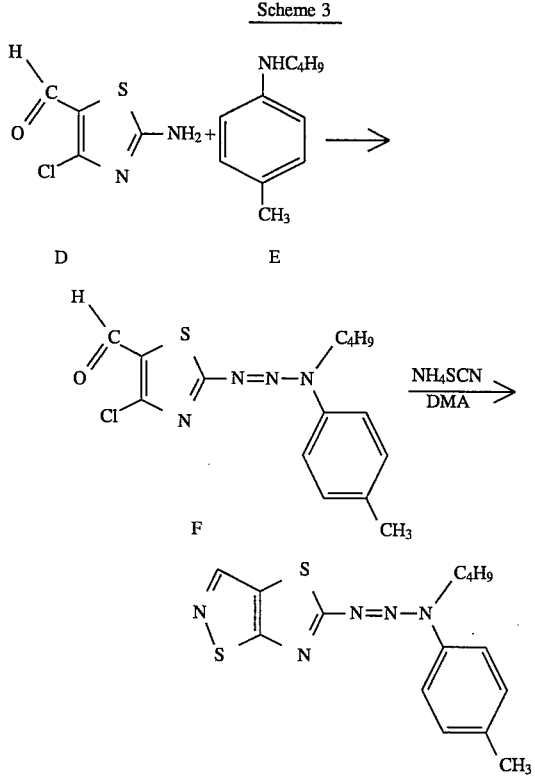

Preparation of dye F 58 ml of nitrosylsulfuric acid is added over one hour to a suspension of 41 g of product D in 320 g of phosphoric acid at 0° C. The orange sirup is stirred for one hour. This sirup is added at −5° C. to a solution of 41 g of product E in 400 ml of THF, 400 ml of acetic acid and 500 g of ice. The suspension is stirred for 30 minutes. A saturated solution of 700 g of sodium acetate trihydrate in water is added over one hour and stirred for 30 minutes. 1000 ml of water is added and the precipitated dye is filtered to obtain 75 g of dye F.

Preparation of dye T.3

3.4 g (0.01 mole) of dye F and 2.2 g (0.03 mole) of $NH_4SCN$ are stirred in 15 ml of dimethylacetamid. The reaction mixture is heated for 4 hours at 90° C. After cooling the reaction mixture is poured into a mixture of water/methanol. The precipitate is filtered and purified by column chromatography to obtain 1 g of dye T.3 (m.p. 147° C.). The structure of dye T.3 is confirmed by $^1$H-NMR analysis (20° C., 300 MHz, $CDCl_3$) : 0.98 ppm ($CH_3$); 1.44 ppm ($CH_2$); 1.81 ppm ($CH_2$); 4.40 ppm ($CH_2$—N): 2.41 ppm ($CH_3$): 7.27, 7.38 ppm (phenyl); 8.54 ppm (H-C=N): 7.27 ppm ($CHCl_3$).

EXAMPLE 5

Synthesis of 1,4-Dithia-2,6-diaza-pentalen-5-ylamin (Compound G)

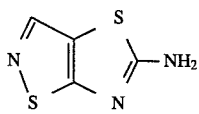

Compound G

Compound G can be prepared according to scheme 4. Compound H an be prepared according to U.S. Pat. No. 4,395,544.

Scheme 4

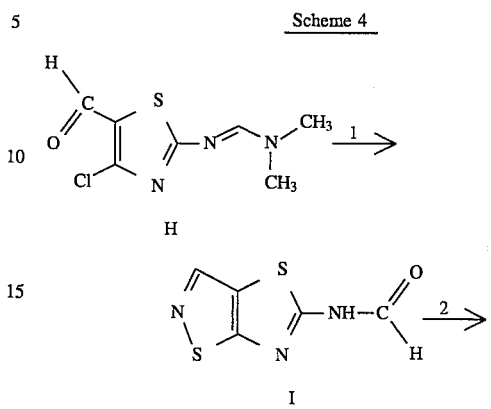

Compound G

Step 1

21.7 g (0.1 mole) of compound H and 22.8 g (0.3 mole) of $NH_4SCN$ are suspensed in 100 ml of dimethylacetamide. The reaction mixture is stirred at 72° C. for two hours and poured into 500 g of ice/water. A 5% solution of $NaHCO_3$ in water is added until neutral. The precipitate is filtered and stirred for one hour in 100 ml of methanol: 1000 ml of dichloromethane is added and the solution is refluxed for 30 minutes. Celite is added and the solution is filtered, concentrated under reduced pressure and purified by column chromatography to obtain 2 g of pure compound I. The structure of compound I is confirmed by $^1$H-NMR analysis (20° C., $d_6$-DMSo, 2.50 ppm, 300 MHz) : 8.78 ppm (H—C=N); 8.63 ppm (CHO): 12.80 ppm (NH); and by $^{13}$C-NMR analysis (20° C., $d_6$-DMSo, 39.5 ppm, 75 MHz):

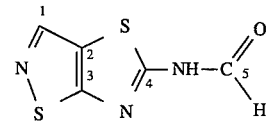

| Atom | $^{13}$C | |
|---|---|---|
| 1 | 148.8 | $^1J(C_1,H_1) = 193$ Hz |
| 2 | 128.4 | |
| 3 | 170.6 | |
| 4 | 164.5 | |
| 5 | 160.7 | $^1J(C_5,H_5) = 210$ Hz |

Step 2

220 mg of compound I is dissolved in 1.5 ml of ethanol. 1.0 ml of 0.5 N HCl-solution in water is added. The solution is refluxed for one hour. After cooling, the solution is neutralized with a 5% sodium bicarbonate solution until pH=7. The precipitate is filtered, washed with water and dried to obtain 135 mg of compound G (86%). The structure of compound G is confirmed by $^1$H-NMR analysis (20° C., $d_6$-DMSo, 2.50 ppm, 300 MHz) : 8.43 ppm (H—C=N): 7.98 ppm ($NH_2$), and by $^{13}$C-NMR analysis ($d_6$-DMSo, 20° C., 75 MHz: 39.5 ppm):

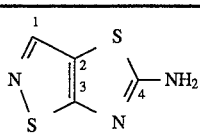

| Atom | $^{13}C$ | |
|---|---|---|
| 1 | 147.6 | $^1J(C_1,H_1) = 190$ Hz |
| 2 | 123.1 | |
| 3 | 173.8 | |
| 4 | 176.06 | |

The new heterocyclic compound 1,4-dithia-2,6-diazapentalen-5-ylamin (compound G) can be used as an intermediate in the synthesis of dyes, especially azo dyes, spectrally sensitizing dyes and pigments, and in the synthesis of plant protection agents and pharmaceutically active compounds.

EXAMPLE 6

Synthesis of dye A.3 through diazotisation of compound G 0.33 ml of nitrosylsulfuric acid is added over 10 minutes to a suspension of 240 mg (1.5 mmole) of compound G at −5° C. The solution is stirred at −3° C. for one hour and added to a solution of 310 mg (1.5 mmole) of N,N-dibutylaniline in 15 ml of sulfuric acid (5% w/w in water) and 1.5 ml of THF. After stirring for one hour the green precipitate is filtered, washed twice with water, washed twice with a 1% sodium bicarbonate solution, washed with water and dried at 40° C. The compound is purified by column chromatography: 350 mg of dye A.3 is obtained (62.5%).

The dyes mentioned in table 3 are prepared from compound G according to the procedure described in EP94201905.

The dyes can be used as filter dyes e.g. for silver halide colour photographic materials and also as antihalation dyes.

The dyes corresponding to the general formula (I) defined above can be used in inkjer printing, resistive ribbon printing, in inks e.g. for laser applications, in textile, in lacquers, and in paints. They can also be used for transfer printing on fabrics and for constructing filter array elements. According to a preferred embodiment of the present invention the dyes are used in the dye layer of a dye-donor element for thermal dye sublimation transfer.

To improve the stability of the dyes to light, the use of a metal complex of the dye e.g. a Ni or Co complex is also effective.

The dye layer is formed preferably by adding the dye, a polymeric binder medium, and other optional components to a suitable solvent or solvent mixture, dissolving or dispersing the ingredients to form a coating composition that is applied to a support, which may have been provided first with an adhesive or subbing layer, and dried.

The dye layer thus formed has a thickness of about 0.2 to 5.0 μm. preferably 0.4 to 2.0 μm. and the amount ratio of dye to binder ranges from 9:1 to 1:3 by weight, preferably from 2:1 to 1:2 by weight.

As polymeric binder the following can be used : cellulose derivatives, such as ethyl cellulose, hydroxyethyl cellulose, ethylhydroxy cellulose, ethylhydroxyethyl cellulose, hydroxypropyl cellulose, methyl cellulose, cellulose nitrate, cellulose acetate formate, cellulose acetate hydrogen phthalate, cellulose acetate, cellulose acetate propionate, cellulose acetate butyrate, cellulose acetate pentanoate, cellulose acetate benzoate, cellulose triacetate: vinyl-type resins and derivatives, such as polyvinyl alcohol, polyvinyl acetate, polyvinyl butyral, copolyvinyl butyral-vinyl acetal-vinyl alcohol, polyvinyl pyrrolidone, polyvinyl acetoacetal, polyacrylamide; polymers and copolymers derived from acrylates and acrylate derivatives, such as polyacrylic acid, polymethyl methacrylate and styrene-acrylate copolymers; polyester resins; polycarbonates; copolystyrene-acrylonitrile; polysulfones; polyphenylene oxide; organosilicones, such as polysiloxanes; epoxy resins and natural resins, such as gum arabic. Preferably, the binder for the dye layer of the present invention comprises cellulose acetate butyrate of copolystyrene-acrylonitrile.

The dyes in accordance with the present invention may be used in admixture with other known dyes for thermal sublimation printing. In particular they can be used in combination with tricyano- and dicyanovinyl dyes as disclosed in EP 92203566, EP 92203208 and with malononitrile dimer derived dyes as disclosed in EP-A-400706. The present dyes may also be used in admixture with azo dyes e.g. disperse azo dyes, anthraquinone dyes, indoaniline dyes, azomethine dyes. Examples of dyes that can be used in combination with the dyes of the present invention are disclosed in e.g. EP 92203979, EP 209,990, EP 209,991, EP 216,483, EP 218,397, EP 227,095, EP 227,096, EP 229,374, EP 235,939, EP 247,737, EP 257,577, EP 257,580, EP 258,856, EP 279,330, EP 279,467, EP 285,665, EP 400,706, U.S. Pat. Nos. 4,743,582, 4,753,922, 4,753,923, 4,757,046, 4,769,360, 4,771,035, 5,026,677, JP 84/78,894, JP 84/78, 895, JP 84/78,896, JP 84/227,490, JP 84/227,948, JP 85/27, 594, JP 85/30,391, JP 85/229,787, JP 85/229,789, JP 85/229, 790, JP 85/229,791, JP 85/229,792, JP 85/229,793, JP 85/229,795, JP 86/41,596, JP 86/268,493, JP 86/268,494, JP 86/268,495, and JP 86/284,489, U.S. Pat. Nos. 4,839,336, 5,168,094, 5,147,844, 5,177,052, 5,175,069, 5,155,088, 5,166,124, 5,166,129, 5,166,128, 5,134,115, 5,132,276, 5,132,275, 5,132,274, 5,1320273, 5,132,268, 5,132,267, 5,126,314, 5,126,313, 5,126,312, 5,126,311, 5,134,116, 4,975,410, 4,885,272, 4,886,029, etc..

The coating layer may also contain other additives, such as curing agents, preservatives, organic or inorganic fine particles, dispersing agents, antistatic agents, defoaming agents, viscosity-controlling agents, these and other ingredients have been described more fully in EP 133,011, EP 133,012, EP 111,004, and EP 279,467.

Any material can be used as the support for the dye-donor element provided it is dimensionally stable and capable of withstanding the temperatures involved, up to 400° C. over a period of up to 20 msec, and is yet thin enough to transmit heat applied on one side through to the dye on the other side to effect transfer to the receiver sheet within such short periods, typically from 1 to 10 msec. Such materials include polyesters such as polyethylene terephthalate, polyamides, polyacrylates, polycarbonates, cellulose esters, fluorinated polymers, polyethers, polyacetals, polyolefins, polyimides, glassine paper and condenser paper. Preference is given to a support comprising polyethylene terephthalate. In general, the support has a thickness of 2 to 30 μm. The support may also be coated with an adhesive or subbing layer, if desired.

The dye layer of the dye-donor element may be coated on the support or printed thereon by a printing technique such as gravure process.

A dye barrier layer comprising a hydrophilic polymer may also be employed between the support and the dye layer of the dye-donor element to enhance the dye transfer densities by preventing wrong-way transfer of dye backwards to the support. The dye barrier layer may contain any hydrophilic material that is useful for the intended purpose. In general, good results have been obtained with gelatin, polyacrylamide, polyisopropyl acrylamide, butyl methacrylate grafted gelatin, ethyl methacrylate-grafted gelatin, ethyl acrlate-grafted gelatin, cellulose monoacetate, methylcellulose, polyvinyl alcohol, polyethyleneimine, polyacrylic acid, a mixture of polyvinyl alcohol and polyvinyl acetate, a mixture of polyvinyl alcohol and polyacrylic acid, or a mixture of cellulose monoacetate and polyacrylic acid. Suitable dye barrier layers have been described in e.g. EP 227091 and EP 228065. Certain hydrophilic polymers, e.g. those described in EP 227091, also have an adequate adhesion to the support and the dye layer, so that the need for a separate adhesive or subbing layer is avoided. These particular hydrophilic polymers used in a single layer in the dye-donor element thus perform a dual function, hence are referred to as dye-barrier/subbing layers.

Preferably the reverse side of the dye-donor element has been coated with a slipping layer to prevent the printing head from sticking to the dye-donor element. Such a slipping layer would comprise a lubricating material such as a surface active agent, a liquid lubricant, a solid lubricant or mixtures thereof, with or without a polymeric binder. The surface-active agents may be any agents known in the art such as carboxylates, sulfonates, phosphates, aliphatic amine salts, aliphatic quaternary ammonium salts, polyoxyethylene alkyl ethers, polyethylene glycol fatty acid esters, fluoroalkyl C2–C20 aliphatic acids. Examples of liquid lubricants include silicone oils, synthetic oils, saturated hydrocarbons and glycols. Examples of solid lubricants include various higher alcohols such as stearyl alcohol, fatty acids and fatty acid esters. Suitable slipping layers have been described in e.g. EP 138483, EP 227090, U.S. Pat. No. 4,567,113, 4,572,860, 4,717,711. Preferably the slipping layer comprises a styrene-acrylonitrile copolymer or a styrene-acrylonitrile-butadiene copolymer or a mixture thereof or a polycarbonate as described in EP-A-527520 as binder and a polysiloxane-polyether copolymer or polytetrafluoroethylene or a mixture thereof as lubicrant in an amount of 0.1 to 10% by weight of the binder or binder mixture.

The support for the receiver sheet that is used with the dye-donor element may be a transparent film of e.g. polyethylene terephthalate, a polyether sulfone, a polyimide, a cellulose ester or a polyvinyl alcohol-co-acetal. The support may also be a reflective one such as baryta-coated paper, polyethylene-coated paper or white polyester i.e. white-pigmented polyester. Blue-coloured polyethylene terephthalate film can also be used as support.

To avoid poor adsorption of the transferred dye to the support of the receiver sheet or receiver element this support must be coated with a special surface, a dye-image-receiving layer, into which the dye can diffuse more readily. The dye-image-receiving layer may comprise, e.g. a polycarbonate, a polyurethane, a polyester, a polyamide, polyvinyl chloride, polystyrene-co-acrylonitrile, polycaprolactone or mixtures thereof. The dye-image receiving layer may also comprise a heat-cured product of poly(vinylchloride/co-vinylacetate/co-vinylalcohol) and polyisocyanate. Suitable dye-receiving layers have been described in e.g. EP 133011, EP 133012, EP 144247, EP 227094, EP 228066.

In order to improve the light-fastness and other stabilities of recorded images, UV absorbers, singlet oxygen quenchers such as HALS-compounds (Hindered Amine Light Stabilizers) and/or antioxidants can be incorporated into the receiving layer.

The dye layer of the dye-donor element or the dye-image-receiving layer of the receiver sheet may also contain a releasing agent that aids in separating the dye-donor element from the receiving sheet after transfer. The releasing agents can also be incorporated in a separate layer on at least part of the dye layer and/or of the dye-image-receiving layer. Suitable releasing agents are solid waxes, fluorine- or phosphate-containing surface-active agents and silicone oils. Suitable releasing agents have been described in e.g. EP 133012, JP 85/19138 and EP 227092.

The dye-donor elements according to the invention are used to form a dye transfer image, which process comprises placing the dye layer of the dye-donor element in face-to-face relation with the dye-image-receiving layer of the receiver sheet or receiver element and image-wise heating preferably from the back of the dye-donor element. The transfer of the dye is accomplished by heating for about several milliseconds at a temperature of 400° C.

When the process is performed for but one single color, a monochrome dye transfer image is obtained. A multicolor image can be obtained by using a dye-donor element containing three or more primary colour dyes and sequentially performing the process steps described above for each colour. After the first dye has been transferred, the elements are peeled apart. The above sandwich of dye-donor element and receiver sheet is formed on three occasions during the time when heat is applied by the thermal printing head. After the first dye has been transferred, the elements are peeled apart. A second dye-donor element (or another area of the dye-donor element with a different dye area) is then brought in register with the dye-receiving element and the process is repeated. The third colour and optionally further colours are obtained in the same manner.

In addition to thermal heads, laser light, infrared flash or heated pens can be used as the heat source for supplying heat energy. Thermal printing heads that can be used to transfer dye from the dye-donor elements of the present invention to a receiver sheet are commercially available. In case laser light is used, the dye layer or another layer of the dye element has to contain a compound that absorbs the light emitted by the laser and converts it into heat e.g. carbon black.

Alternatively, the support of the dye-donor element may be an electrically resistive ribbon consisting of e.g. a multilayer structure of a carbon loaded polycarbonate coated with a thin aluminum film. Current is injected into the resistive ribbon by electrically adressing a printing head electrode resulting in highly localized heating of the ribbon beneath the relevant electrode. The fact that in this case the heat is generated directly in the resistive ribbon and that it is thus the ribbon that gets hot leads to an inherent advantage in printing speed using the resistive ribbon/electrode head technology compared to the thermal head technology, according to which the various elements of the thermal head get hot and must cool down before the head can move to the next printing position.

The following examples illustrate the invention in more detail without limiting, however, the scope thereof.

EXAMPLE 7

The absorption maxima ($\lambda_{max}$) and extinction maxima ($\epsilon_{max}$) of some dyes identified below were determined in methanol. The results are listed in table 4.

TABLE 4

| Dye | $\lambda_{max}$ (nm) | $\epsilon_{max}$ | m.p. (°C.) |
|---|---|---|---|
| A.3 | 539 | 58707 | 130 |
| A.6 | 540 | 58006 | 112 |
| A.20 | 538 | 54290 | 116 |
| A.15 | 549 | 63124 | 149 |
| A.18 | 543 | 53334 | 186 |
| A.25 | 575 | 33889 | 125 |
| A.19 | 532 | 52456 | 85 |
| A.21 | 567 | 59423 | 245 (dec) |
| T.3 | 390 | 27186 | 147 |

EXAMPLE 8

Receiver sheets were prepared by coating a subbed polyethylene terephthalate film having a thickness of 175 μm with a dye-image-receiving layer from a solution in ethyl methyl ketone of 3,6 g/m² of poly(vinyl chloride/co-vinyl acetate/co-vinyl alcohol) (Vinylite™ VAGD supplied by Union Carbide), 0,336 g/m² of diisocyanate (Desmodur™ VL supplied by Bayer AG), and 0.2 g/m² of hydroxy-modified polydimethylsiloxane (Tegomer™ H SI 2111 supplied by Goldschmidt).

Dye-donor elements for use according to thermal dye sublimation transfer were prepared as follows:

A solution comprising 0.5% by weight of dye and 0.5% by weight of copoly(styrene-acrylonitrile) (Luran™ 388S, supplied by BASF, Germany) as binder in ethyl methyl ketone was prepared.

From this solution a dye layer having a wet thickness of 100 um was coated on a polyethylene terephthalate film support having a thickness of 6 μm and carrying a conventional subbing layer. The resulting dye layer was dried by evaporation of the solvent.

The opposite side of the film support was coated with a subbing layer of a copolyester comprising ethylene glycol, adipic acid, neopentyl glycol, terephthalic acid, isophthalic acid, and glycerol.

The resulting subbing layer was covered with a solution in methyl ethyl ketone of 0.5 g/m² of a polycarbonate having the following structural formula to form a heat-resistant layer:

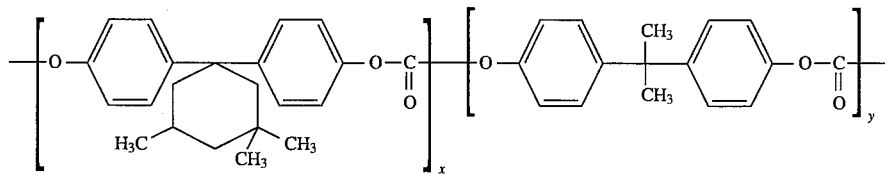

wherein x=55 mol % and y=45 mol %.

Finally, a top layer of polyether-modified polydimethylsiloxane (Tegoglide™ 410, Goldschmidt) was coated from a solution in isopropanol on the resulting heat-resistant polycarbonate layer.

The dye-donor element was printed in combination with a receiver sheet in a Mitsubishi colour video printer CP100E.

The receiver sheet was separated from the dye-donor element and the colour density value of the recorded image was measured in reflection by means of a Macbeth TR 924 densitometer in the red, green, and blue region in Status A mode.

The results are listed in Table 5.

TABLE 5

| Dye No. | Max. Dens. | Spectral absorption in Status A filter behind | | |
|---|---|---|---|---|
| | | Red | Green | Blue |
| T.3 | 163 | 12 | 15 | 150 |
| A.3 | 279 | 28 | 150 | 29 |
| A.6 | 284 | 29 | 150 | 31 |
| A.15 | 213 | 43 | 150 | 29 |
| A.18 | 207 | 33 | 150 | 33 |
| A.19 | 191 | 35 | 150 | 34 |
| A.20 | 236 | 28 | 150 | 30 |
| A.25 | 137 | 137 | 99 | 24 |

EXAMPLE 9

Composition of high density black-coloured dye mixtures according to the present invention.

Receiver sheets were prepared as described in example 8.

Black dye-donor elements were prepared as follows:

The amounts of dyes as indicated in the following Table 6 were added each time to 10 ml of a solution of 0.5% by weight of poly(styrene-co-acrylonitrile) (Luran™ 388S, supplied by BASF Germany) in ethyl methyl ketone. The resulting black-coloured dye mixtures were coated, printed, and evaluated as described in the above example 8, with the proviso that the densities are given in transmission.

The results of the tests are listed in the following Table 6. The prior art dyes C-cyan and C-yellow having the following structural formulae were used in the tests.

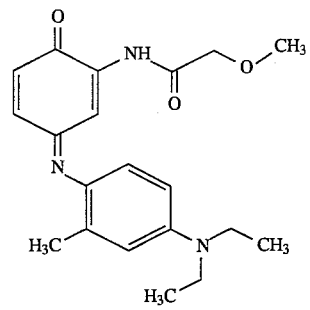

C-cyan 1

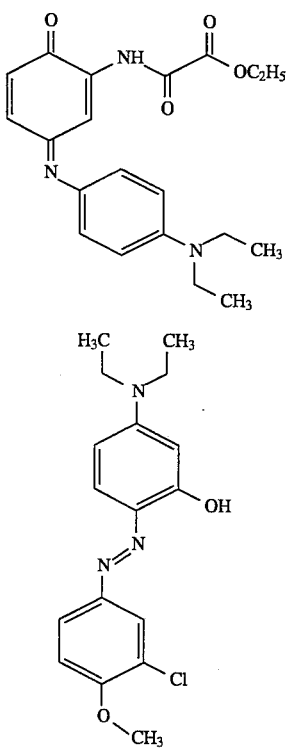

These dyes can be prepared as described in U.S. Pat. No. 5,169,828, corresponding EP 453,020 and EP94201725.

TABLE 6

| Test No. | Dye | Mount of dye in mg | Spectral absorption in Status A behind filter | | | |
|---|---|---|---|---|---|---|
| | | | Red | Green | Blue | Visual |
| 1 | C-cyan 1 | 30 | 120 | 239 | 163 | 188 |
| | A.18 | 50 | | | | |
| | C-yellow | 30 | | | | |
| 2 | C-cyan 2 | 40 | 160 | 211 | 169 | 199 |
| | A.18 | 40 | | | | |
| | C-yellow | 30 | | | | |
| 3 | C-cyan 2 | 30 | 130 | 290 | 181 | 203 |
| | A.3 | 50 | | | | |
| | C-yellow | 30 | | | | |
| 4 | C-cyan 1 | 30 | 121 | 293 | 180 | 198 |
| | A.6 | 50 | | | | |
| | C-yellow | 30 | | | | |
| 5 | C-cyan 2 | 40 | 152 | 225 | 160 | 182 |
| | A.20 | 40 | | | | |
| | C-yellow | 30 | | | | |

The results listed in Table 6 show that by means of dye-donor elements incorporating a dye mixture comprising a heterocyclic azo dye according to the present invention transferred dye images can be made, which have high black density values.

I claim:

1. Dye-donor element for use according to thermal dye sublimation transfer, said dye-donor element comprising a support having thereon a dye layer comprising a polymeric binder and a dye corresponding to the following general formula (I):

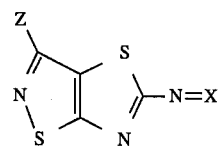

wherein:

Z represents hydrogen or a substituent,

X represents N-R or

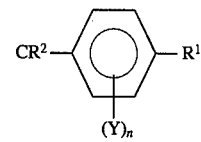

R represents $NR^3R^4$;

$R^1$ represents $NR^3R^4$ $OR^{12}$ or $SR^{12}$;

$R^2$ represents hydrogen cyano $COR^{13}$, $CO^2R^{13}$, $CONR^{14}R^{15}$, $SO_2R^{16}$;

$R^3$ and $R^4$ each independently represent hydrogen, an alkyl group, an alkynyl group, an aryl group, an alkenyl group, a heterocyclic group or $R^3$ and $R^4$ together with the atoms to which they are attached represent the atoms necessary to complete a ring or $R^3$ and/or $R^4$ and one of the Y-substituents together with the atoms to which they are attached represent the necessary atoms to form a 5- or 6- membered, fused-on heterocyclic ring;

Y represents a substituent:

n represents 0, 1, 2, 3 or 4, the substituents being the same or different when n is greater than 1 or two or more Y substituents can form an annelated ring system:

$R^{12}$, $R^{13}$, $R^{14}$ and $R^{15}$ each independently represent hydrogen, in alkyl group, an alkenyl group, an alkynyl group, an aryl group, a heterocyclic ring or $R^{14}$ and $R^{15}$ together with the atoms to which they are attached represent the necessary atoms to form a 5- or 6-membered ring or $R^{13}$ or $R^{14}$ or $R^{15}$ or $R^{14}$ and $R^{15}$ together with one of the Y-substituents and the atoms to which they are attached represent the necessary atoms to form a 5- or 6-membered fused-on heterocyclic ring;

$R^{16}$ represents hydroxy, an alkoxy group, an aryloxy group, $NR^{17}R^{18}$, an aryl group or an alkyl group, an alkenyl group, an alkynyl group, or $R^{16}$ together with one of the Y-substituents and the atoms to which they are attached represent the necessary atoms to form a 5- or 6-membered fused-on heterocyclic ring:

$R^{17}$ and $R^{18}$ each independently represent hydrogen, an alkyl group, an alkenyl group, an alkynyl group, an aryl group, a heterocyclic ring or $R^{17}$ and $R^{18}$ together with the atoms to which they are attached represent the necessary atoms to form a 5- or 6-membered ring.

2. A dye donor element according to claim 1 wherein said dye corresponds to one of the following formulas:

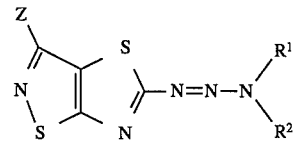

-continued

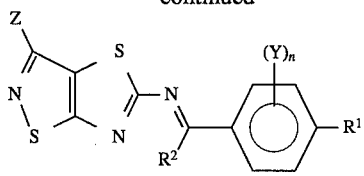 Ic wherein Z, $R^1$, $R^2$, Y and n have the same meaning as defined in the general formula (I) of claim 1.

3. Dye-donor element for use according to thermal dye sublimation transfer, said dye-donor element comprising a support having thereon a dye layer comprising a polymeric binder and a dye corresponding to the following general formula (I):

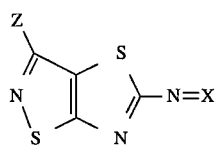 (I)

wherein:

Z represents hydrogen or a substituent,

X represents N-R and R represents the residue of an aromatic coupling compound E-Q wherein Q is a group displaceable by a diazotised amine.

4. A dye donor element according to claim 1 or 3 wherein said dye layer comprises a repeating sequence of at least two dye frames and at least one of said dye frames comprising a dye according formula (I).

5. A dye-donor element according to claim 3, wherein E corresponds to the following formula:

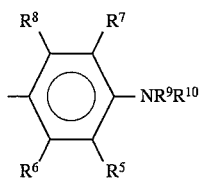 (II)

$R^5$, $R^6$, $R^7$, and $R^8$ each independently represent hydrogen, an alkyl group, an alkenyl group, an alkynyl group, an aryl group, an alkoxy group, an alkylthio group, an arylthio group, an aryloxy group, a carbamoyl group, a sulfamoyl group, hydroxy, SH, an amino group, a halogen, $NO_2$, CN, $NHSO_2R^{11}$, $NHCOR^{11}$, $OSO_2R^{11}$, $OCOR^{11}$, $COR^{11}$ or $R^7$ and $R^8$ together and/or $R^5$ and $R^6$ together with the atoms to which they are attached represent the necessary atoms to complete a ring or $R^7$ and $R^9$ together with the atoms to which they are attached and/or $R^5$ and $R^{10}$ together with the atoms to which they are attached represent the necessary atoms to form a heterocyclic ring;

$R^{11}$ represents an alkyl group, an alkenyl group, an alkynyl group, an an aryl group, an alkyloxy group, an aryloxy group, an alkylthio group, an arylthio group, an amino group or a heterocyclic group;

$R^9$ and $R^{10}$ each independently represent hydrogen, an alkyl group, an alkenyl group, an alkynyl group, an aryl group, a heterocyclic group or $R^9$ and $R^{10}$ together with the atoms to which they are attached represent the necessary atoms to form a heterocyclic ring.

6. A dye donor element according to claim 4 wherein said dye layer comprises a sequence of at least three dye frames having respectively a yellow, magenta and cyan color.

7. A dye donor element according to claim 3 wherein said dye corresponds to the formula:

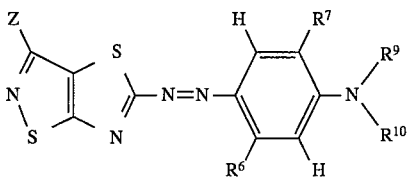 Ib wherein Z represents hydrogen or a substituent, $R^6$ and $R^7$ each independently represent hydrogen, an alkyl group, an alkenyl group, an alkynyl group, an aryl group, an alkoxy group, an alkylthio group, an arylthio group, an aryloxy group, a carbamoyl group, a sulfamoyl group, hydroxy, SH, an amnio group, a halogen, $NO_2$, CH, $NHSO_2R^{11}$, $NHCOR^{11}$, $OSO_2R^{11}$, $OCOR^{11}$, $COR^{11}$ or $R^7$ and $R^9$ together with the atoms to which they are attached represent the necessary atoms to form a heterocyclic ring; $R^{11}$ represents an alkyl group, an alkenyl group, an alkynyl group, an aryl group, an alkyloxy group, an aryloxy group, an alkylthio group, and arylthio group, an amino group or a heterocyclic group; $R^9$ and $R^{10}$ each independently represent hydrogen, an alkyl group, an alkenyl group, an alkynyl group, an aryl group, a heterocyclic group or $R^9$ and $R^{10}$ together with the atoms to which they are attached represent the necessary atoms to form a heterocyclic ring.

8. A method for making an image according to the thermal dye transfer process comprising the steps of:

placing the dye layer of a dye donor element comprising a support having thereon a dye layer comprising a polymeric binder and a dye corresponding to the following general formulae (I):

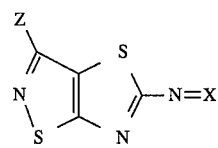 (I)

wherein:

Z represents hydrogen or a substituent,

X represents N-R or

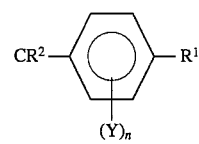

R represents $NR^3R^4$;

$R^1$ represents $NR^3R^4$, $OR^{12}$ or $SR^{12}$;

$R^2$ represents hydrogen, cyano, $COR^{13}$, $CO_2R^{13}$, $CONR^{14}R^{15}$, $SO_2R^{16}$;

$R^3$ and $R^4$ each independently represent hydrogen, an alkyl group, an alkynyl group, an aryl group, an alkenyl group, a heterocyclic group or $R^3$ and $R^4$ together with the atoms to which they are attached represent the atoms necessary to complete a ring or $R^3$ and/or $R^4$ and one of the Y-substituents together with the atoms to which they are attached represent the necessary atoms to form a 5- or 6-membered, fused-on heterocyclic ring;

Y represents a substituent;

n represents 0, 1, 2, 3 or 4, the substituents being the same or different when n is greater than 1 or two or more Y substituents can form an annelated ring system;

$R^{12}$, $R^{13}$, $R^{14}$ and $R^{15}$ each independently represent hydrogen, an alkyl group, an alkenyl group, an alkynyl group, an aryl group, a heterocyclic ring or $R^{14}$ and $R^{15}$ together with the atoms to which they are attached represent the necessary atoms to form a 5- or 6-membered ring or $R^{13}$ or $R^{14}$ or $R^{15}$ or $R^{14}$ and $R^{15}$ together with one of the Y-substituents and the atoms to which they are attached represent the necessary atoms to form a 5- or 6-membered fused-on heterocyclic ring:

$R^{16}$ represents hydroxy, an alkoxy group, an aryloxy group, $NR^{17}R^{18}$, an aryl group or an alkyl group, an alkenyl group, an alkynyl group, or $R^{16}$ together with one of the Y-substituents and the atoms to which they are attached represent the necessary atoms to form a 5- or 6-membered fused-on heterocyclic ring;

$R^{17}$ and $R^{18}$ each independently represent hydrogen, an alkyl group, an alkenyl group, an alkynyl group, an aryl group, a heterocyclic ring or $R^{17}$ and $R^{18}$ together with the atoms to which they are attached represent the necessary atoms to form a 5- or 6-membered ring in face-to-face relationship with a dye-image receiving layer of a receiver sheet:

image-wise heating a thus obtained assemblage and separating said receiver sheet from said dye donor element.

9. A method according to claim 8 wherein said dye corresponds to one of the following formulas:

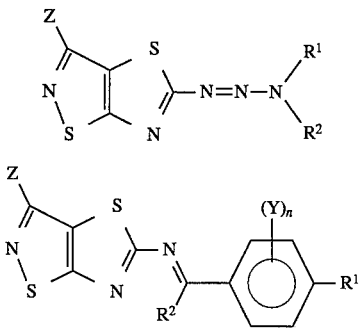

wherein Z, $R^1$, $R^2$, $R^6$, $R^7$, $R^{10}$, Y and n have the same meaning as defined in the general formula (I) of claim 1.

10. A method for making an image according to the thermal dye transfer process comprising the steps of:

placing the dye layer of a dye donor element comprising a support having thereon a dye layer comprising a polymeric binder and a dye corresponding to the following general formula (I):

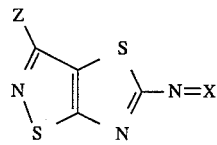

wherein:

Z represents hydrogen or a substituent,

X represents N-R and R represents the residue of an aromatic coupling compound E-Q wherein Q is a group displaceable by a diazotised amine in face to face relationship with a dye-image receiving layer of a receiver sheet; image-wise heating a thus obtained assemblage; and separating said receiver sheet from said dye donor element.

11. A method according to claim 10 wherein E corresponds to the following formula:

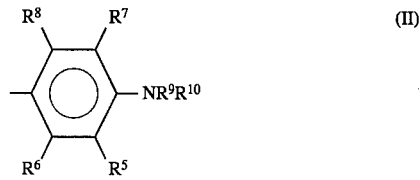

$R^5$, $R^6$, $R^7$, and $R^8$ each independently represent hydrogen, an alkyl group, an alkenyl group, an alkynyl group, an aryl group, an alkoxy group, an alkylthio group, an arylthio group, an aryloxy group, a carbamoyl group, a sulfamoyl group, hydroxy, SH, an amino group, a halogen, $NO_2$, CN, $NHSO^2R^{11}$, $NHCOR^{11}$, $OSO_2R^{11}$, $OCOR^{11}$, $COR^{11}$ or $R^7$ and $R^8$ together and/or $R^5$ and $R^6$ together with the atoms to which they are attached represent the necessary atoms to complete a ring or $R^7$ and $R^9$ together with the atoms to which they are attached and/or $R^5$ and $R^{10}$ together with the atoms to which they are attached represent the necessary atoms to form a heterocyclic ring;

$R^{11}$ represents an alkyl group, an alkenyl group, an alkynyl group, an an aryl group, an alkyloxy group, an aryloxy group, an alkylthio group, an arylthio group, an amino group or a heterocyclic group;

$R^9$ and $R^{10}$ each independently represent hydrogen, an alkyl group, an alkenyl group, an alkynyl group, an aryl group, a heterocyclic group or $R^9$ and $R^{10}$ together with the atoms to which they are attached represent the necessary atoms to form a heterocyclic ring.

12. A method according to claim 10 wherein said dye corresponds to the formula:

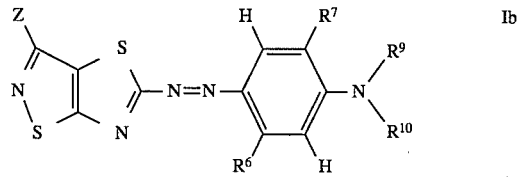

wherein Z represents hydrogen or a substituent, $R^6$ and $R^7$ each independently represent hydrogen, an alkyl group, an alkenyl group, an alkynyl group, an aryl group, an alkoxy group, an alkylthio group, an arylthio group, an aryloxy group, a carbamoyl group, a sulfamoyl group, hydroxy, SH, an amino group, a halogen, $NO_2$, CN, $NHSO_2R^{11}$, $NHCOR^{11}$, $OSO_2R^{11}$, $OCOR^{11}$, $COR^{11}$ or $R^7$ and $R^9$ together with the atoms to which they are attached represent the necessary atoms to form a heterocyclic ring; $R^{11}$ represents an alkyl group, an alkenyl group, an alkynyl group, an aryl group, an alkyloxy group, an aryloxy group, an alkylthio group, and arylthio group, an amino group or a heterocyclic group; $R^9$ and $R^{10}$ each independently represent hydrogen, an alkyl group, an alkenyl group, an alkynyl group, an aryl group, a heterocyclic group or $R^9$ and $R^{10}$ together with the atoms to which they are attached represent the necessary atoms to form a heterocyclic ring.

* * * * *

UNITED STATES PATENT AND TRADEMARK OFFICE
CERTIFICATE OF CORRECTION

PATENT NO. : 5,589,316

DATED : December 31, 1996

INVENTOR(S) : Luc Vanmaele

It is certified that error appears in the above-identified patent and that said Letters Patent is hereby corrected as shown below:

On title page,
2nd Column, 8th line, "aryl group, an" should read --aryl group,--;

Column 2, bridging lines 41-42, "$COR^{13}CO_2R^{13}CONR^{14}R^{15}SO_2R^{16}$" should read --$COR^{13}$, $CO_2R^{13}$, $CONR^{14}R^{15}$, $SO_2R^{16}$--;

Column 2, line 64, "one the" should read --one of the--;

Column 3, line 44, "halogen $NO_2$" should read --halogen, $NO_2$--;

Column 7, line 64, under "Scheme 1" insert "B";

Column 8, line 7, "1H-NMR" should read --$^1$H-NMR--;

Column 11, line 42, "inkier" should read --inkjet--;

Column 12, line 65, "as" should read --as a--;

Column 18, line 20, "hydrogen cyano" should read --hydrogen, cyano,--;

UNITED STATES PATENT AND TRADEMARK OFFICE
CERTIFICATE OF CORRECTION

PATENT NO. : 5,589,316

DATED : December 31, 1996

INVENTOR(S) : Luc Vanmaele

It is certified that error appears in the above-identified patent and that said Letters Patent is hereby corrected as shown below:

Column 18, line 38, "in alkyl" should read --an alkyl--;

Column 18, lines 60-65, in formula Ia, "$R^1$" should read --$R^3$--;

Column 18, line 60-65, in formula Ia "$R^2$" should read --$R^4$--;

Column 19, line 8, after "$R^2$," insert --$R^3$, $R^4$,--;

Column 20, line 13, "CH" should read --CN--;

Column 22, line 16, "$NHSO^2R^{11}$" should read --$NHSO_2R^{11}$--.

Signed and Sealed this

Eleventh Day of August 1998

*Attest:*

BRUCE LEHMAN

*Attesting Officer*  *Commissioner of Patents and Trademarks*